United States Patent
Fisher et al.

(10) Patent No.: US 9,052,323 B2
(45) Date of Patent: Jun. 9, 2015

(54) OSMOLYTE MIXTURE FOR PROTEIN STABILIZATION

(75) Inventors: Mark T. Fisher, Shawnee Mission, KS (US); Hiroo Katayama, Kansas City, KS (US)

(73) Assignee: The University of Kansas, Lawrence, KS (US)

( * ) Notice: Subject to any disclaimer, the term of this patent is extended or adjusted under 35 U.S.C. 154(b) by 628 days.

(21) Appl. No.: 12/870,236

(22) Filed: Aug. 27, 2010

(65) Prior Publication Data

US 2011/0053795 A1    Mar. 3, 2011

Related U.S. Application Data

(60) Provisional application No. 61/237,451, filed on Aug. 27, 2009.

(51) Int. Cl.
| | | |
|---|---|---|
| *C40B 30/10* | (2006.01) | |
| *G01N 33/68* | (2006.01) | |
| *C12N 9/96* | (2006.01) | |

(52) U.S. Cl.
CPC ............ *G01N 33/6803* (2013.01); *C40B 30/10* (2013.01); *C12N 9/96* (2013.01)

(58) Field of Classification Search
None
See application file for complete search history.

(56) References Cited

U.S. PATENT DOCUMENTS

| | | | |
|---|---|---|---|
| 5,474,892 A | 12/1995 | Jakob et al. | |
| 5,663,304 A | 9/1997 | Builder et al. | |
| 5,756,672 A | 5/1998 | Builder et al. | |
| 5,776,724 A | 7/1998 | Hartl et al. | |
| 6,270,954 B1 | 8/2001 | Welch et al. | |
| 6,887,682 B2 | 5/2005 | Fisher et al. | |
| 7,799,535 B1 * | 9/2010 | Lindquist | 435/7.31 |
| 2003/0212248 A1 | 11/2003 | Furman | |
| 2005/0196824 A1 | 9/2005 | Fisher et al. | |
| 2006/0018918 A1 | 1/2006 | Chang | |
| 2006/0252917 A1 | 11/2006 | Bulaj | |

OTHER PUBLICATIONS

Voziyan et al, Jrnl. of Pharmaceutical Sciences, 89, 8, Aug. 2000, 1036-45.*

* cited by examiner

*Primary Examiner* — Christian Boesen
(74) *Attorney, Agent, or Firm* — Maschoff Brennan, PLLC

(57) ABSTRACT

An osmolyte composition comprising 4 M glycerol and 4M urea for stabilizing previously transient protein folding intermediates as long-lived stable forms. A method to search for other possible stabilizing osmolyte mixtures using a screening array is also provided. These additional osmolyte mixtures may complement or augment the successful 4M glycerol/4 M urea mixture.

17 Claims, 13 Drawing Sheets

Unfold protein in denaturant (GnHCl, Urea, etc.)

Dilute into 4 M urea/4 M glycerol with excess GroEL in solution or immobilized on NHS beads Replace urea/glycerol with refolding buffer using ultrafiltration (GroEL capture step)

Add folding osmolyte and ATP to concentrated GroEL-protein complex

Refold and elute or separate concentrated refolded protein

OSMOLYTE MIXTURE FOR PROTEIN STABILIZATION

CROSS-REFERENCE TO RELATED APPLICATIONS

This application is based on and claims priority to U.S. Provisional Application Ser. No. 61/237,451, filed on Aug. 27, 2009 which is hereby incorporated herein by reference.

STATEMENT REGARDING FEDERALLY SPONSORED RESEARCH OR DEVELOPMENT

This invention was made with government support under contract R42 GS077735-01 awarded by the National Institutes of Health and contract MCB-0445926 awarded by the National Science Foundation. The government has certain rights in the invention.

FIELD OF THE INVENTION

This invention relates to compositions of matter and methods for in vitro protein folding. More particularly, the present invention is directed to osmolyte compositions capable of stabilizing protein intermediates and preventing protein aggregation. The present invention is also directed to methods for optimizing protein folding, as well as to aid in the screening for optimal protein stabilizing/folding solution conditions.

BACKGROUND OF THE INVENTION

Efficient refolding of proteins in vitro is an important problem in protein structural analysis and biotechnological manufacturing of pharmaceutical products. Because of their inherent ability to rapidly overexpress proteins to high yields, bacterial systems are the organisms of choice for protein mass production. Unfortunately, overexpression of foreign and, especially, mutant proteins often leads to the development of large intracellular aggregates or inclusion bodies (Rudolph et al., *In vitro folding of inclusion body proteins*, FASEB J. 10 49-56 (1996); Guise et al., *Protein folding in vivo and renaturation of recombinant proteins from inclusion bodies*, Mol. Biotechnol. 6 53-64 (1996), the disclosures of which are incorporated herein by reference). In some cases, the proper intracellular folding of the overexpressed proteins can be enhanced by lowering the cell growth temperature, co-expressing molecular chaperones, or introducing low molecular weight additives (Kujau et al., *Expression and secretion of functional miniantibodies McPC603scFvDhlx in cell wall-less L-form strains of Proteus mirabilis and E. coli*, Appl. Microbiol. Biotechnol. 49 51-58 (1998); Tate et al., *Molecular Chaperones Stimulate the Functional Expression of the Cocaine-sensitive Serotonin Transporter*, J. Biol-Chem. 274 17551-17558 (1999); Minning et al., *Functional expression of Rhizopus oryzae lipase in Pichia pastoris: high-level production and some properties*, J. Biotechnol. 66 147-156 (1998), the disclosures of which are incorporated herein by reference). More often, however, investigators are forced to rely on in vitro folding methods to denature (also known as "deactivate") and then refold (also known as "reactivate") aggregated proteins. A number of in vitro approaches have been developed to minimize protein aggregation and enhance proper refolding. Among those are: (1) the addition of osmolytes and denaturants to refolding buffer (Tate et al., *Molecular Chaperones Stimulate the Functional Expression of the Cocaine-sensitive Serotonin Transporter*, J. Biol-Chem. 274 17551-17558 (1999); Plaza-del-Pino et al., *An osmolyte effect on the heat capacity change for protein folding*, Biochemistry 34 8621-8630 (1995); Frye et al., *The kinetic basis for the stabilization of staphylococcal nuclease by xylose*, Protein. Sci. 6 789-793 (1997), the disclosures of which are incorporated herein by reference); (2) the use of the combinations of different molecular chaperones (Thomas et al., *Molecular chaperones, folding catalysts, and the recovery of active recombinant proteins from E. coli. To fold or to refold*, Appl. Biochem. Biotechnol. 66 197-238 (1997); Buchberger, A., Schroder, H., Hesterkamp, T., Schonfeld, H. J., and Bukau, B. (1996) J. Mol. Biol. 261, 328-233; Veinger et al., *The Small Heat-shock Protein IbpB from Escherichia coli Stabilizes Stress-denatured Proteins for Subsequent Refolding by a Multichaperone Network*, J. Biol. Chem. 273, 11032-11037 (1998), the disclosures of which are incorporated herein by reference); (3) immobilization of folding proteins to matrices and matrix-bound chaperonins (Stempfer, G., Holl-Neugebauer, B., and Rudolph, R. (1996) Nat. Biotechnol. 14, 329-334; Proc. Natl. Acad. Sci. USA 94, 3576-3578; Preston, N. S., Baker, D. J., Bottomley, S. P., and Gore, M. G. (1999) Biochim. Biophys. Acta 1426, 99-109, the disclosures of which are incorporated herein by reference); and (4) utilization of folding catalysts such as protein disulfide isomerase and peptidyl-prolyl cis-trans isomerase (Altamirano, M. M., Garcia, C., Possani, L. D., and Fersht, A. R. (1999) Nat. Biotechnol. 17, 187-191, the disclosure of which is incorporated herein by reference). While the latter investigators (Altamirano et al., 1999) used a truncated monomer of the chaperonin, prominent researchers in the field have since demonstrated that the best functional construction of the chaperonin is its native oligomeric form (Wang, J D, Michelitsch M D, and Weissman J S (1998) "GroEL-GroES-mediated protein folding requires and intact central cavity" Proc. Natl. Acad. Sci. USA 95, 12163-12168; Weber F, Keppel F, Georgopoulos C, Hayer-Hartl M K, Hartl F U. *The oligomeric structure of GroEL/GroES is required for biologically significant chaperonin function in protein folding*, Nat Struct Biol. 5(11):977-85). Because of the diversity of the protein folding mechanisms, there has been no universal procedure for protein folding and folding conditions have to be optimized for each specific protein of interest. Therefore, there is always a need for new and more versatile folding techniques. This invention involves a novel protein folding procedure that utilizes a novel stabilizing osmolyte composition useful for stabilizing protein intermediates. Chaperonins, particularly the functional and tight binding oligomeric chaperonins (e.g., GroE), can be added in order to facilitate complete folding of the protein to its native functional form.

Because of its ability to bind many different protein folding intermediates, it was thought that the bacterial GroE chaperonin system could provide a general method to refold misfolded proteins. Chaperonin GroEL is a tetradecamer of identical 57 kDa subunits that possesses two large hydrophobic sites capable of binding to transient hydrophobic protein folding intermediates. The hydrophobic binding site undergoes the multiple cycles of exposure and burial driven by the ATP binding and hydrolysis and the co-chaperonin GroES binding and dissociation. Accordingly, the protein folding intermediates can undergo multiple rounds of binding to and release from the GroEL until they achieve the correctly folded state (for review, see Fenton, W. A. and Horwich, A. L. (1997) Protein Sci. 6, 743-760, the disclosure of which is incorporated herein by reference). Besides simple prevention of nonproductive aggregation, chaperonins may also influence the conformation of the folding intermediates, actively diverting them to a productive folding pathway (Fedorov, A. N. and Baldwin, T. O. (1997) J. Mol. Biol. 268, 712-723; Shtilerman, M., Lorimer, G., and Englander, S. W. (1999) Science 284, 822-825, the disclosures of which are incorporated herein by reference). However, despite the general nature of chaperonin-protein interactions, there are many proteins that, for reasons that are currently unknown, cannot fold correctly from the bacterial chaperonin system.

The addition of osmolytes often results in an observed increase in stability of the native structure for some proteins. The stabilization effect is observed with various osmolytes and small electrolytes such as sucrose, glycerol, trimethylamine N-oxide (TMAO), potassium glutamate, arginine and betaine (Wang, A. and Bolen, D. W. (1997) Biochemistry 36, 9101-9108; De-Sanctis, G., Maranesi, A., Ferri, T., Poscia, A., Ascoli, F., and Santucci, R. (1996) J. Protein. Chem. 15, 599-606; Chen, B. L. and Arakawa, T. (1996) J. Pharm. Sci. 85, 419-426; Zhi, W., Landry, S. J., Gierasch, L. M., and Srere, P. A. (1992) Protein Science 1, 552-529, the disclosures of which are incorporated herein by reference). This effect is based on the exclusion of osmolytes from hydration shells and crevices on protein surface (Timasheff, S. N. (1992) Biochemistry 31 9857-9864, the disclosure of which is incorporated herein by reference) or decreased solvation (Parsegian, V. A., Rand, R. P., and Rau D. (1995) Methods. Enzymol. 259 43-94, the disclosure of which is incorporated herein by reference). In a series of quantitative studies, Wang and Bolen have shown that the osmolyte-induced increase in protein stability is due to a preferential burial of the polypeptide backbone rather than the amino acid side chains (Wang, A. and Bolen, D. W. (1997) Biochemistry 36 9101-9108; Bolen et al., *The Osmophobic Effect: Natural Selection of a Thermodynamic Force in Protein Folding*, J. Mol. Biol. Vol. 310 955-963 (2001)). Because native protein conformations are stabilized, proper folding reactions are also enhanced in the presence of osmolytes (Frye, K. J. and Royer, C. A. (1997) Protein. Sci. 6 789-793; Kumar, T. K., Samuel, D., Jayaraman, G., Srimathi, T., and Yu, C. (1998) Biochem. Mol. Biol. Int. 46 509-517; Baskakov, I. and Bolen, D. W. (1998) J. Biol. Chem. 273 4831-4834, the disclosures of which are incorporated herein by reference). Osmolytes usually affect protein stability and folding at physiological concentration range of 1-4 M (Yancey, P. H., Clark, M. E., Hand, S. C., Bowlus, R. D., and Somero, G. N. (1982) Science 217 1214-1222, the disclosure of which is incorporated herein by reference). However, it is apparent that the degree of stabilization depends on both the nature of the osmolyte and the protein substrate (Sola-Penna, M., Ferreira-Pereira, A., Lemos, A. P., and Meyer-Fernandes, J. R. (1997) Eur. J. Biochem. 248 24-29, the disclosure of which is incorporated herein by reference) and, in some instances, the initial aggregation reaction can actually accelerate in the presence of some strong folding osmolytes such as TMAO (Voziyan, P. A. and Fisher M. T. (2000) Protein Science, Vol 9 2405-2412).

Fisher et al., U.S. Pat. No. 6,887,682, which is incorporated by reference, found that folding of a denatured polypeptide could be improved by first forming a chaperonin-polypeptide complex, and then adding an osmolyte to promote folding. Despite the advances set forth in the Fisher '682 patent, improved compositions of matter and methods for stabilizing and folding denatured proteins are needed.

SUMMARY OF THE INVENTION

The present invention is directed to a novel stabilizing osmolyte composition for the stabilization of partially denatured proteins and to an improved process for folding of a completely denatured protein by first forming stabilized partially denatured intermediates. It was surprisingly discovered that partially unfolded proteins prone to aggregation remain stable in high concentrations of urea and glycerol. In addition, GroEL remains in its tetradecameric form in high concentrations of urea and glycerol.

The present invention is also directed to a method for the rapid identification of the optimal protein stabilizing osmolyte compositions to achieve maximal yields of correctly folded protein. In particular, the initial off-pathway aggregation is avoided through formation of stable protein intermediates in the urea/glycerol system (or other test stabilizing osmolyte compositions), such that the solution favors the maximum binding of the substrate to chaperonin (GroEL) when it is added to the system. More specifically, completely denatured/unfolded proteins are added to a series of different test stabilizing osmolyte solutions ("stabilizing array"), and after a time delay, a chaperonin is applied and the protein intermediates are captured by the chaperonin. A folding osmolyte (and ATP) is then added to the system as generally set forth in the Fisher '682 patent, and the system is assayed for functional activity of the protein. The array provides a method for identifying the most efficient stabilizing/folding conditions for the protein in question.

Therefore, it is an object of this invention to provide an in vitro protein folding process for preventing large-scale protein misfolding and aggregation.

It is a further object to provide a protein folding process that enables one to concentrate aggregation-prone folding intermediates as a stable non-aggregating form.

It is another object of this invention to provide a protein folding process that rapidly screens for the best long term stabilization conditions where protein folding intermediates can be stabilized without loss due to aggregation prior to folding.

To accomplish the above and related objects, this invention may be embodied in the detailed description that follows, together with the appended drawings and claims.

DETAILED DESCRIPTION OF PREFERRED EMBODIMENT

Figure 1:
FIG. 1 is a flow chart showing an overview of the protein folding process of the present invention, including the step of stabilizing the protein intermediates using an osmolyte solution of glycerol and urea.
Figure 1:
Figure 1:
Figure 1:

As used herein, "chaperonin" is defined as any protein complex that binds to an unfolded or partially unfolded polypeptide to facilitate the folding of said polypeptide to its biologically active state either independently or with the assistance of other elements. This definition specifically includes but is not limited to chaperonin systems from bacteria and bacteriophages, including mesophiles and thermophilic chaperonins. Similarly, as used herein, chaperonin includes but is not limited to chaperonins in any native or modified state, for example, single ring chaperonins, glutaldehyde cross-linked chaperonins, or other chemically modified chaperonins.

As used herein, the term "conformation" is used to define the spatial arrangement of amino acid residues of a protein/peptide. The term "conformation" is equivalent to and interchangeable with tertiary structure, three-dimensional structure, spatial arrangement, and all other applicable terms and phrases known and used by one of skill in the art. A protein can potentially assume an exceeding large number of conformations. Under physiological conditions, a protein usually folds properly and adopts the native structure with a well defined three dimensional conformation. Unlike the native protein, a denatured protein includes a collection of non-native conformation isomers that exist in a state of equilibrium. Non-native conformation isomers of denatured proteins are rich in number and varied in shape. They represent a vast resource of biological molecules that have remained untapped for their potential applications in the prevention, diagnosis, and treatment of human diseases. As discussed below, isomers of denatured protein are potential resource for vaccine development. Isomers of denatured proteins have been shown to involve in the development of numerous neurodegenerative diseases. They are potential targets for disease diagnosis and intervention. Isomers of denatured proteins are also potential candidates to be developed as antagonists.

As used herein, the term "denaturant" generally refers to those chaotropic compounds or materials which, in aqueous solution and in suitable concentrations are capable of changing the spatial configuration or conformation of proteins through alterations at the surface thereof, either through altering, for example, the state of hydration, the solvent environment, or the solvent-surface interaction. Examples of such denaturants include urea, guanidine hydrochloride, sodium thiocyanate, and detergents, such as SDS and Triton. It does not include such drastic and irreversible denaturing procedures as high temperature (typically greater than 60° C.) or high acidity (pH typically less than 1).

As used herein, "osmolyte" refers to an agent that lends osmolality to the buffered solution or affects hydration or surface tension. Examples include polyols and sugars such as glycerol, erythritol, arabitol, sorbitol, mannitol, xylitol, mannisidomannitol, glycosyl glycerol, glucose, fructose, sucrose, trehalose, and isofluoroside; polymers such as dextrans, levans, and polyethylene glycol; and some amino acids and derivatives thereof such as glycine, alanine, alpha-alanine, arginine, proline, taurine, betaine, octopine, glutamate, sarcosine, y-aminobutyric acid, and trimethylamine N-oxide ("TMAO"), as described more fully in Yancey et al., Science, 217 1214-1222 (1982) and Schein, Bio/Technology, 8 308-315 (1990). The present invention utilizes two types of osmolytes: a stabilizing osmolyte mixture (e.g., urea and glycerol) that are used to stabilize partially denatured or partially unfolded proteins, and refolding osmolytes which are added after formulation on the polypeptide-chaperonin complex which facilitate refolding of the protein to its nature form.

As used herein, the terms "polypeptide" or "protein" are used interchangeably refer to a polymer of amino acids and does not refer to a specific length. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring.

As used herein, "unfolded," "denatured," and "inactive" are defined interchangeably to mean the characteristic of polypeptides which are no longer biologically active due, at least in part, to not being in their native conformation. As such, the terms include partially folded proteins, chemically unfolded proteins, thermally denatured proteins, pressure unfolded proteins, and oxidatively damaged proteins. An unfolded polypeptide may thus be completely or partially unfolded. "Completely" unfolded or denatured polypeptides have no secondary or tertiary structure, while "partially" unfolded or denatured polypeptides have elements of native secondary and/or tertiary structure.

FIG. 1 is an overview of the protein folding process of the present invention. In general, the target protein is first placed in solution with a suitable denaturant. Next, the completely unfolded protein is placed in a solution containing high concentrations of the stabilizing osmolytes of the present invention in order to form a stabilized protein composition comprising stable partially folded non-native conformation isomers of the target protein and the stabilizing osmolyte composition. The term "non-native conformation isomers" describes polypeptides that assume a secondary, tertiary, and/or quaternary structure that is not the complete native equivalent. The term "stable" means that the non-native conformation isomer does not proceed down folding pathways that results in protein aggregates or irreversibly misfolded forms. Thus, use of the stabilizing osmolyte composition of the present invention results in stable non-native conformation isomers of the protein that are substantially free of protein aggregates (e.g., refractile bodies or inclusion bodies typically visible under a phase contrast microscope) yet does not completely acquire a native fold. Typically, the completely denatured protein exists in rapid equilibrium with the heterogeneous partially unfolded non-native conformation isomers.

The preferred stabilizing osmolytes that form the stabilizing osmolyte composition are urea and glycerol. Thus, in one aspect, the stabilized protein composition comprises the completely denatured protein in equilibrium with the stable partially unfolded non-native conformation isomers, urea, and glycerol. For example, the stabilized protein composition typically comprises 0.1 to 50 µM of protein, 0.5 to 8 M urea, and 0.5 to 6 M glycerol. In a preferred aspect, the stabilized protein composition comprises 1 to 10 µM of protein, 1 to 5 M urea, and 1 to 5 M glycerol. The most preferred stabilizing osmolyte composition illustrated in examples presented herein comprises 3 to 5 M glycerol and 4 to 5 M urea.

The stabilized protein composition is useful with and without the addition of a chaperonin, such as GroEL. For example, the stabilized non-native conformation isomers may have enough secondary, tertiary, or quaternary structure to function as antigens and induce an immune response or provide a binding surface for specific antibodies. The compositions and methods of the present invention also relate to the production and application of stabilized non-native conformation isomers, in purified form or in mixture form, as candidates of vaccine development for prevention and treatment of human diseases that are patient specific. For example, multiple isomers, or pools of isomers may be spotted, e.g., subcutaneously, to determine the best immune response. Following the initial inoculation, the best immunogenic isomer or pool of isomers may be used for continued inoculation. Often, the vaccine or immunogenic composition comprising the stabilized non-native conformation isomers may also be provided with one or more adjuvants. The vaccine may be further adapted for intramuscular, intravenous, subcutaneous, pulmonary, oral, ocular, topical, sublingual, intraperitoneal, intraosseal, rectal, vaginal, or intranasal injection.

Non-limiting examples of stabilized non-native conformation isomers useful in the present invention could include the intrinsically disordered class of proteins such as alpha-synuclein, amyloid beta-protein 1-42, and other disease associated proteins such as the prion proteins, CD4, or gp120. More particularly, the isomer may be associated with a conformational disease selected from the group consisting of prion-associated diseases, mad cow disease, scrapie, Creutzfeldt-Jacob disease, familial insomnia, Alzheimer disease, Parkinson disease, alpha1-antitrypsin deficiency, and cystic fibrosis. Alternatively, the protein selected for the production of non-native isomers includes those from pathogenic organisms, proteins associated with auto-immune diseases, cancers, auto-inflammatory diseases, allergies, anaphylaxis, and the like.

Chaperonin (e.g., GroEL) may be simultaneously added to the stabilized protein composition or added after a time delay. Thus, in one aspect, the stabilized and partially unfolded denatured proteins and stabilizing osmolytes (e.g., high concentration urea and glycerol) are combined with excess GroEL in solution or GroEL immobilized on suitable platform. GroEL immobilization (e.g., on N-Hydroxysuccinimide (NHS)-activated Sepharose 4 fast flow beads (Pharmacia-Biotech)) is generally described in Example 10 of Fisher et al., U.S. Published Patent Application No. 2005/196824, which is incorporated by reference.

In order to properly fold the denatured protein and the stabilized partially unfolded non-native conformation isomers into the native form, the methods of Fisher et al., U.S. Published Patent Application No. 2005/196824 are then generally employed. After the chaperonin is added, the stabilizing osmolyte solution (e.g., high concentration urea/glycerol) is replaced with a refolding buffer. The preferred refolding buffer comprises 50 mM Tris-HCl, pH 7.5, 0.5 mM EDTA, 50 mM KCl, 5 mM $MgCl_2$. Ultrafiltration may be used as part of this chaperonin capture step. Ultrafiltration techniques generally rely on the use of polymeric membranes with highly defined pore sizes to separate molecules according to size. The technique relies on the use of centrifugation to drive the migration of the smaller folded protein molecules through the membrane to the filtrate cup with the simultaneous retention of larger molecules in the retentate cup. See generally U.S. Pat. No. 6,357,601 entitled "Ultrafiltration device and method of forming same" and U.S. Pat. No. 4,755,301 entitled "Apparatus and method for centrifugal recovery of retentate."

One or more suitable folding osmolytes are then added to the concentrated chaperonin-protein complex. Preferred folding osmolytes are selected from the group consisting of glycerol, sorbitol, glucose, trehalose, and amino acids.

In the following examples, urea was purchased from ICN Biochemical (Aurora, Ohio), and ATP was from Sigma-Aldrich (St. Louis, Mo.). Glycerol was purchased from Fisher Scientific (Pittsburgh, Pa.). All the above chemicals were over 99% pure. The other chemicals were of analytical grade.

The E. coli chaperonins, GroEL and GroES were isolated from overexpression E. coli strains kindly provided by Drs. Edward Eisenstein and George Lorimer (respectively) and these proteins were purified essentially as described earlier (Fisher, M. T. (1992) Biochemistry 31, 3955-3963; Eisenstein, E., Reddy, P., and Fisher, M. T. (1998) Methods. Enzymol. 290, 119-135; Fisher, M. T. (1994) J. Biol. Chem. 269 13629-13636; Voziyan, P. A. and Fisher M. T. (2000) Protein Science, Vol 9 2405-2412), the disclosures of which are incorporated herein by reference).

EXAMPLE 1

GroEL, is Stable in Urea/Glycerol

Figure 2:
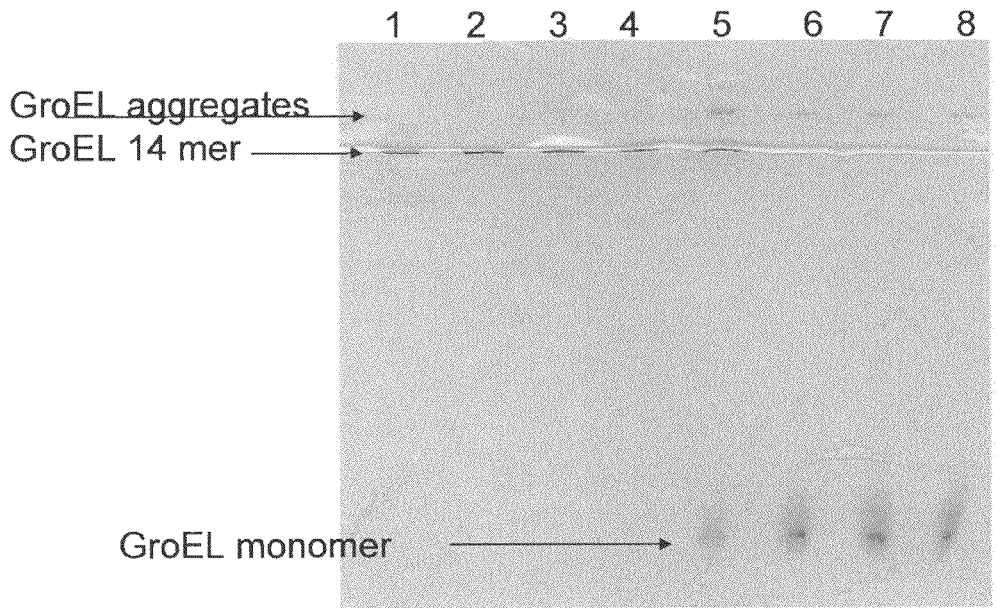
FIG. 2 illustrates the GroEL remains in its functional tetradecameric form in 3 to 7 M urea and 4 M glycerol.

In this example, the stability of GroEL was investigated in two osmolyte solutions. FIG. 2 shows the native gel of GroEL in two different osmolyte solutions (8-25% native gel). Lane 1: 4 M glycerol and 4 M urea. Lane 2: 4 M glycerol and 5 M urea. Lane 3: 4 M glycerol and 6 M urea. Lane 4: 4 M glycerol and 7 M urea. Lane 5: 0.5 M trehalose and 4 M urea. Lane 6: 0.5 M trehalose and 5 M urea. Lane 7: 0.5 M trehalose and 6 M urea. Lane 8: 0.5 M trehalose and 7 M urea. FIG. 2 shows that glycerol is superior in maintaining the functional GroEL oligomer compared to trehalose. Larger aggregates and monomeric GroEL was observed with trehalose/urea solutions.

EXAMPLE 2

Stability of MDH Folding Intermediate

Figure 7:
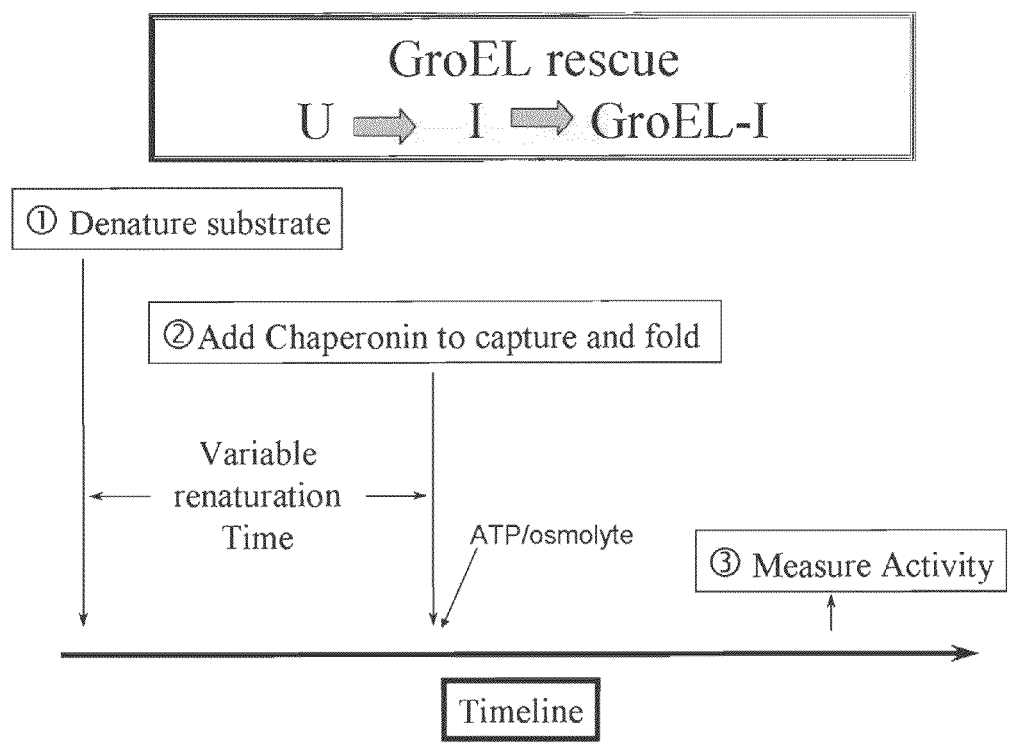
FIG. 7 is a flow diagram illustrating the irreversible misfolding experiments discussed herein and described in Voziyan et al., *Changing the Nature of the Initial Chaperonin Capture Complex Influences the Substrate Folding Efficiency*, J. Biol. Chem. Vol. 273 No. 39, 25073-24078 (1998), which is incorporated by reference.

In this example, an irreversible misfolding kinetic experiment was performed on MDH as generally set forth in Voziyan et al., *Changing the Nature of the Initial Chaperonin Capture Complex Influences the Substrate Folding Efficiency*, J. Biolog. Chem., Vol. 273 No. 39 25073-24078 (1998), which is incorporated by reference. As shown in FIG. 7, introduction of the chaperonin at different times following the initiation of spontaneous refolding allows one to probe how rapidly the protein folding intermediates lose their ability to interact with the chaperonins.

In this example, 10 μM MDH was denatured in 8 M urea for three hours and rapidly diluted 1:10 to 1 μM into either: (1) 4 M glycerol and 4 M urea or (2) refolding buffer solution. Renaturation of 1 μM MDH occurred at physiological temperature (37° C.) for 90 minutes in refolding buffer in the presence of 2 μM GroEL and 5 mM ATP. To determine the lifetime of the MDH folding intermediate, the GroEL capture efficiency was measured by varying the time of GroEL addition to the renaturation solution. After following the scheme outlined in FIG. 1, the MDH activity was measured by diluting an aliquot from the mixture into 1 mM ketomalonic acid, 0.2 mM NADH, 10 mM DTT, and 50 mM TEA, pH 7.5 and following the oxidation of NADH at 340 ml.

Figure 3:
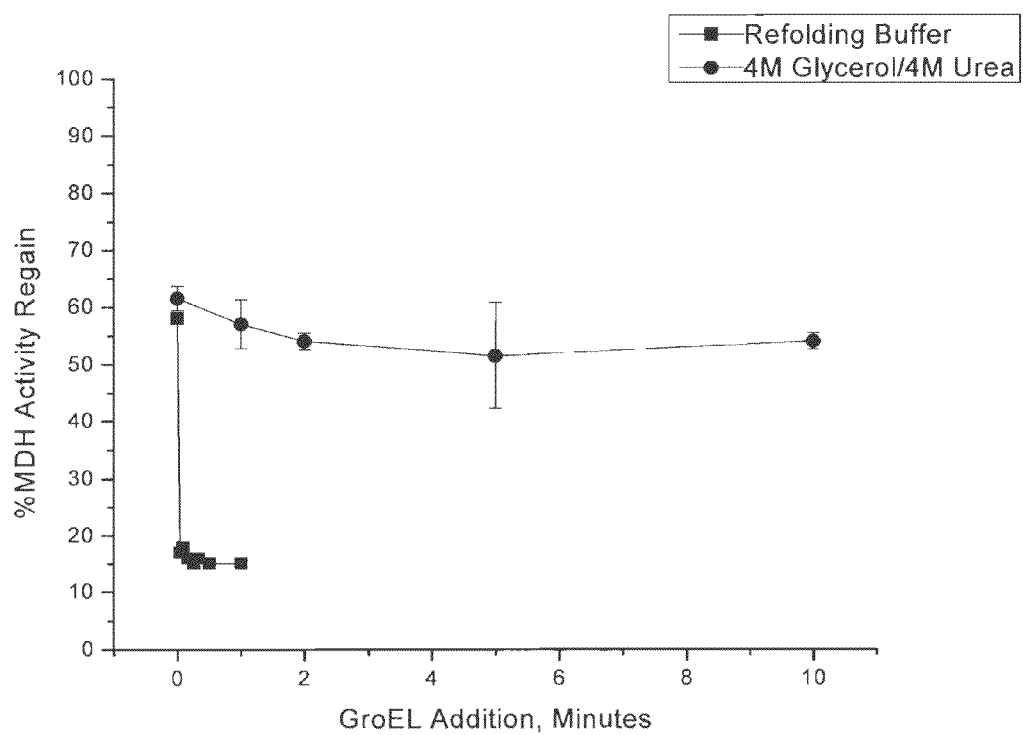
FIG. 3 shows the lifetime of the malate dehydrogenase ("MHD") folding intermediate using an irreversible misfolding kinetics experiment (see FIG. 7).

FIG. 3 shows that the lifetime of the MDH folding intermediate in glycerol/urea was substantially prolonged compared to that of the refolding buffer. Indeed, when using refolding buffer, the protein intermediates immediately and irreversibly misfolded into non-functional proteins. In marked contrast, MDH in glycerol/urea regained over 50% of its enzymatic activity, even when the chaperonin addition was delayed for 10 minutes.

EXAMPLE 3

Stability of CS Folding Intermediate

In this example, an irreversible misfolding kinetic experiment was performed on citrate synthase ("CS"). More specifically, 10 μM CS was denatured in 6 M guanidine hydrochloride for one hour and rapidly diluted 1:10 to 1 μM into either: (1) 4 M glycerol and 4 M urea or (2) refolding buffer solution. Renaturation of 1 μM CS occurred at physiological temperature (37° C.) for 90 minutes in refolding buffer in the presence of 2 μM GroEL and 5 mM ATP. To determine the lifetime of the MDH folding intermediate, the GroEL capture efficiency was measured by varying the time of GroEL addition to the renaturation solution. After following the scheme outlined in FIG. 1, CS activity was measured using the substrates acetyl CoA and oxaloacetate. More specifically, 10 mM acetyl CoA and 40 mM oxaloacetate stock solutions were prepared for the assay. The assay solution contained a final concentration of 100 μM acetyl CoA and 400 μM oxaloacetate. A final CS concentration of 200 nM was added to 1 mL of the assay mixture in a quartz cuvette and activity was measured through the decrease in the absorbance of acetyl CoA at a wavelength of 233 nm.

Figure 4:
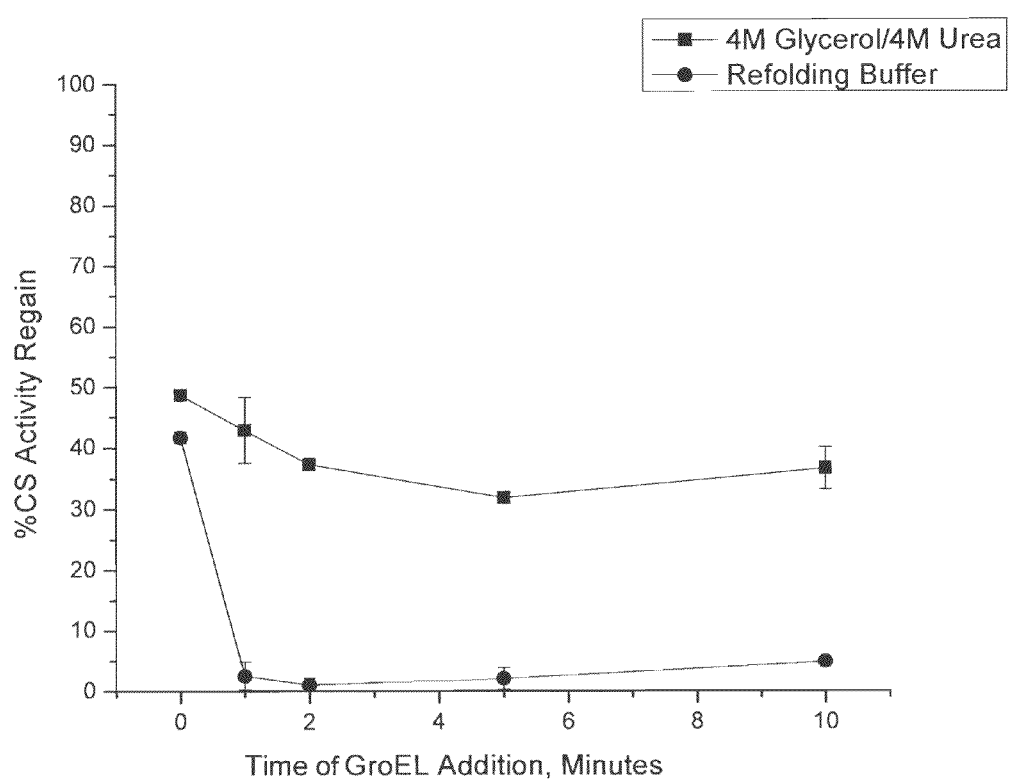
FIG. 4 shows the lifetime of the citrate synthase ("CS") folding intermediate using an irreversible misfolding kinetics experiment (see FIG. 7).

FIG. 4 shows that the lifetime of the CS folding intermediate in glycerol/urea was substantially prolonged compared to that of the refolding buffer. Indeed, when using refolding buffer alone, the protein intermediates immediately and irreversibly misfolded into non-functional proteins. In marked contrast, CS in glycerol/urea regained nearly 40% of its enzymatic activity, even when the chaperonin addition was delayed for 10 minutes.

EXAMPLE 4

Urea Concentration and Stability of MDH Folding Intermediate

In this example, an irreversible misfolding kinetic experiment was performed on MDH in order to assess how urea concentration would affect stability. In this example, 10 μM MDH was denatured in 8 M urea for three hours and rapidly diluted 1:10 to 1 μM into: (1) 4 M glycerol and (2) 3.0 M, 3.5 M, 4.0 M, 4.5 M, and 5.0 M urea. Renaturation of 1 μM MDH occurred at physiological temperature (37° C.) for 90 minutes in refolding buffer in the presence of 2 μM GroEL and 5 mM ATP. After the protein was placed in the glycerol/urea solution, GroEL was added usually in a molar ratio of two GroEL oligomers to 1 mole of protein. The urea/glycerol solution was removed and replaced with refolding buffer using repetitive ultrafiltration methods. Upon forming the tight binding GroEL-protein folding intermediate complex, folding osmolytes (such as 4 M glycerol, 1 M sucrose or 1 M proline, with 4M glycerol being preferred) and 5 mM ATP were added to initiate refolding. MDH activity was measured as set forth in Example 2.

Figure 5:
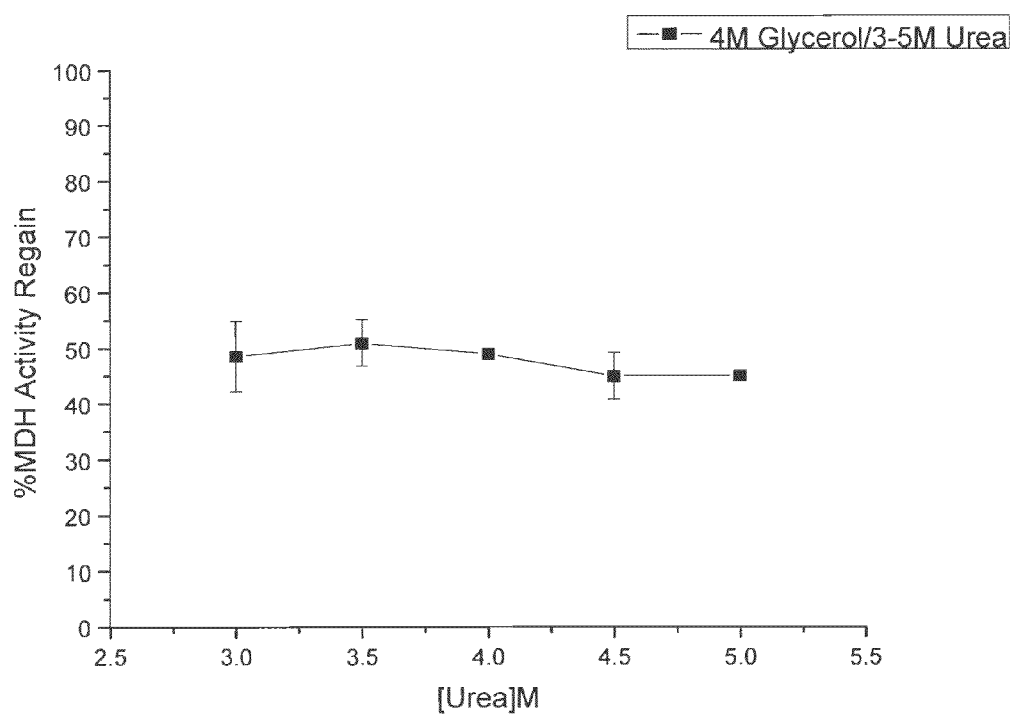
FIG. 5 shows that the MDH folding intermediates could be stabilized with glycerol over a wide range of urea concentrations.

FIG. 5 shows that the lifetime of the MDH folding intermediate in glycerol/urea was substantially prolonged over a wide rang of urea concentrations. MDH in glycerol/urea regained 40-50% of its enzymatic activity over the urea concentrations investigated.

EXAMPLE 5

Urea Concentration and Stability of MDH Folding Intermediate

In this example, an irreversible misfolding kinetic experiment was performed on MDH in order to assess how MDH concentration would affect stability. In this example, 10 μM MDH was denatured in 8 M urea for three hours and rapidly diluted to 1:5 to 1:40 to 0.25 μM to 2.0 μM into 4 M glycerol and 4 M urea. Renaturation of the MDH occurred at physiological temperature (37° C.) for 90 minutes in refolding buffer in the presence of 2:1 GroEL:MDH and 5 mM ATP. After the protein was placed in the glycerol/urea solution, GroEL was added. The urea/glycerol solution was removed and replaced with refolding buffer using repetitive ultrafiltration methods. Upon forming the tight binding GroEL-protein folding intermediate complex, folding osmolytes (such as 4 M glycerol, 1 M sucrose or 1 M proline, with 4M glycerol being preferred) and 5 mM ATP were added to initiate refolding. MDH activity was measured as set forth in Example 2.

Figure 6:
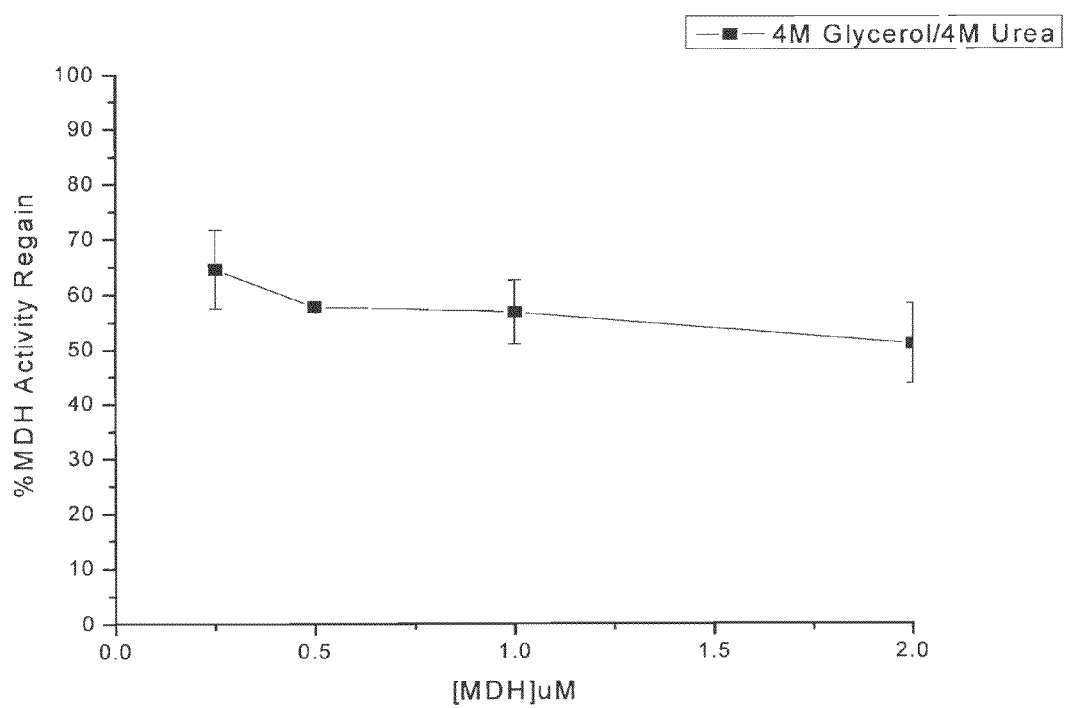
FIG. 6 shows that the MDH folding intermediates could be stabilized with glycerol over a wide range of MDH concentrations.

FIG. 6 shows that the lifetime of the MDH folding intermediate in glycerol/urea was substantially prolonged over a wide rang of protein concentrations. There was a slight concentration-dependent decline in recoverable MDH activity. However, MDH regained 50-70% of its enzymatic activity over the MDH concentrations investigated.

PROPHETIC EXAMPLE 6

Screening

The process of protein folding, in both its theoretical and practical aspects, is currently the focus of intense research.

Despite inherent complexity and variability of protein structures, stabilization of protein intermediates with high concentration glycerol/urea appears to be applicable to a wide variety of proteins. Nonetheless, optimization of the stabilization osmolytes may be performed by employing a rapid and efficient screening procedure to identify the other optimal protein stabilization solutions for specific proteins of interest.

Figure 8:
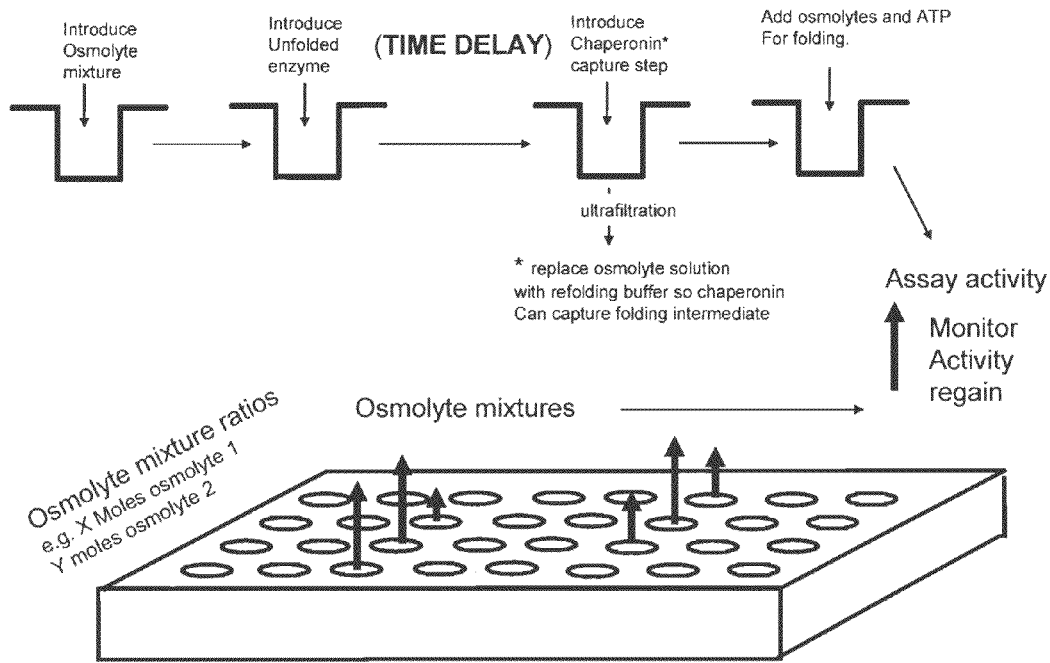
FIG. 8 is a flow chart showing the methodology for a screening approach to identify optimal osmolyte compositions that leads to long term stability of the folding intermediates.

In the present invention, a method for screening for an optimal protein stabilization environment for a partially denatured protein is provided. The overall strategy is set forth in FIG. 8. The screening system uses multiple wells (e.g., 96-well) containing test stabilizing osmolyte systems of interest (e.g., 4 M glycerol and 4 M urea) to identify optimal osmolyte systems of single osmolytes or osmolyte mixtures. In general, the screening method involves providing an array having a plurality of elements with each element having a different test stabilizing osmolyte composition therein (e.g., a multiple well array). Next, a polypeptide in an unfolded state (preferably a protein capable of binding to a chaperonin) is introduced to each element to form a test polypeptide-osmolyte composition. After a predetermined time (typically 1 to 10 minutes, but may be up to 24 hours), a chaperonin is introduced into each well. Preferably, the chaperonin is an oligomeric chaperonin, such as the tetradecamer GroEL. The chaperonin may be introduced in free form or may be immobilized on a collar support or platform that can be inserted into the wells and removed once the folding has been completed. The single collar support may be used to introduce the chaperonin into the multiple elements (e.g., wells) in their entirety or individual collars may be used in conjunction with individual wells. The potentially stabilizing test osmolyte solution is then replaced with refolding buffer so that the chaperonin can bind the folding intermediate much tighter i.e. capture the folding intermediate. A folding osmolyte (and ATP) is then preferably added. Next, the protein from each well is assayed for functional activity. Thus, the optimal stabilizing conditions for the polypeptide are determined.

The test stabilizing osmolyte compositions are preferably those in which the osmolytes are present in high concentrations, typically greater than 1 M, 2 M, 3 M, 4 M, or 5 M, etc depending on osmolyte solubility. Further, when the test osmolyte(s) are present in high concentrations (typically greater than 1 M), they increase the stability of the partially denatured protein and its intermediates greater than the 4 M glycerol and 4 M urea osmolyte composition described herein.

In the screening assay, the chaperonin is preferably from the *Escherichia coli* GroE chaperonin family, such as GroEL. Different test stabilizing osmolyte compositions can be compared in order to identify those, if any, that provide improved stability compared to the "standard" of 4 M glycerol and 4 M urea. Thus, the GroEL capture system provides an exemplary model for the protein stabilizing osmolyte array. Because the GroEL hydrophobic binding site non-specifically binds a wide range of general hydrophobic folding intermediates, the high affinity GroEL species, generated by removing any bound nucleotide, can accommodate and hold an extremely large number of different protein substrates. Not only can GroEL bind a large number of different folding intermediates, it can also stabilize these substrates against aggregation and the folding substrates remain bound to the chaperonin in a foldable form for a relatively long period of time. The high affinity nucleotide-free GroEL is an efficient and stable capture system for folding intermediates, preventing or arresting off-pathway aggregation by sequestering transient kinetic folding intermediates. In some ways, the chaperonin can be compared to a non-specific antibody that binds folding intermediates typically with subnanomolar binding affinities. Once the intermediate is captured, the folding substrate is easily released from GroEL in a controlled manner.

EXAMPLE 7

Characterization of Folding Intermediates

Figure 9:
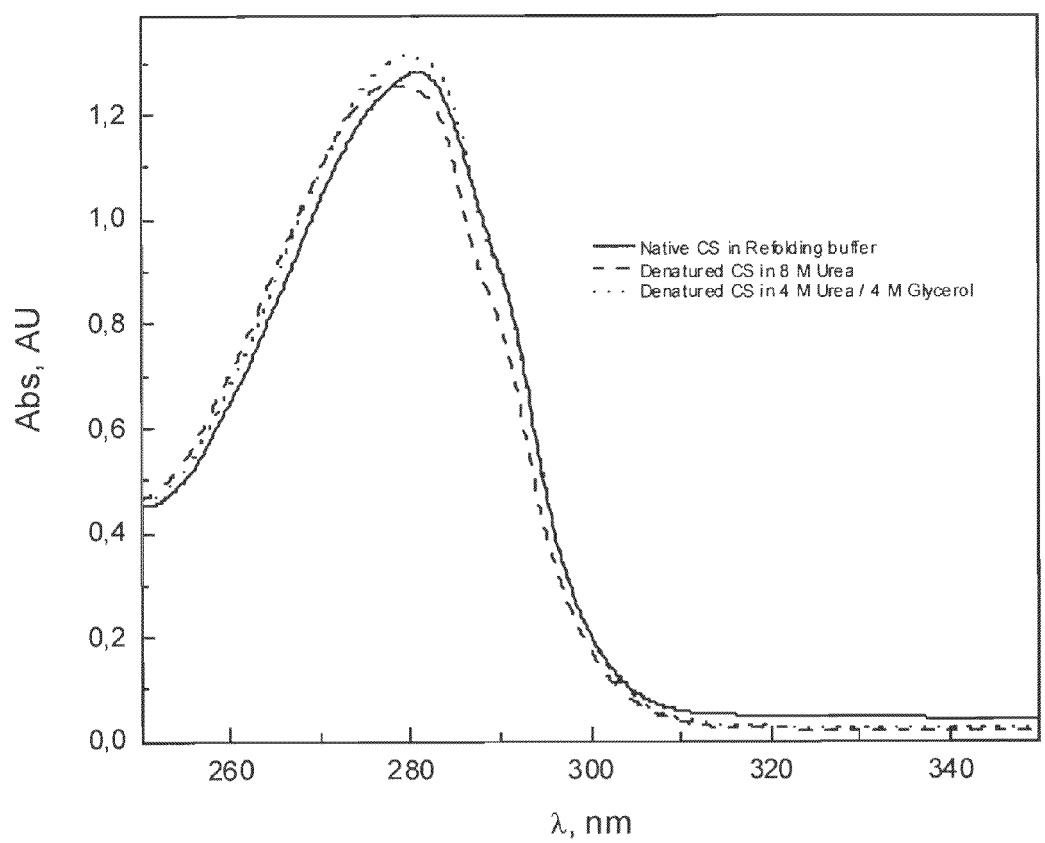
FIG. 9 is an absorbance spectra of citrate synthase in refolding buffer (solid line), in 8 M Urea—buffered (dashed line), and in mixture of 4 M Urea and 4 M Glycerol—buffered (dotted line). Protein concentration in the samples is 1 uM, pH of the buffer and osmolyte mixtures is 7.5.
Figure 10:
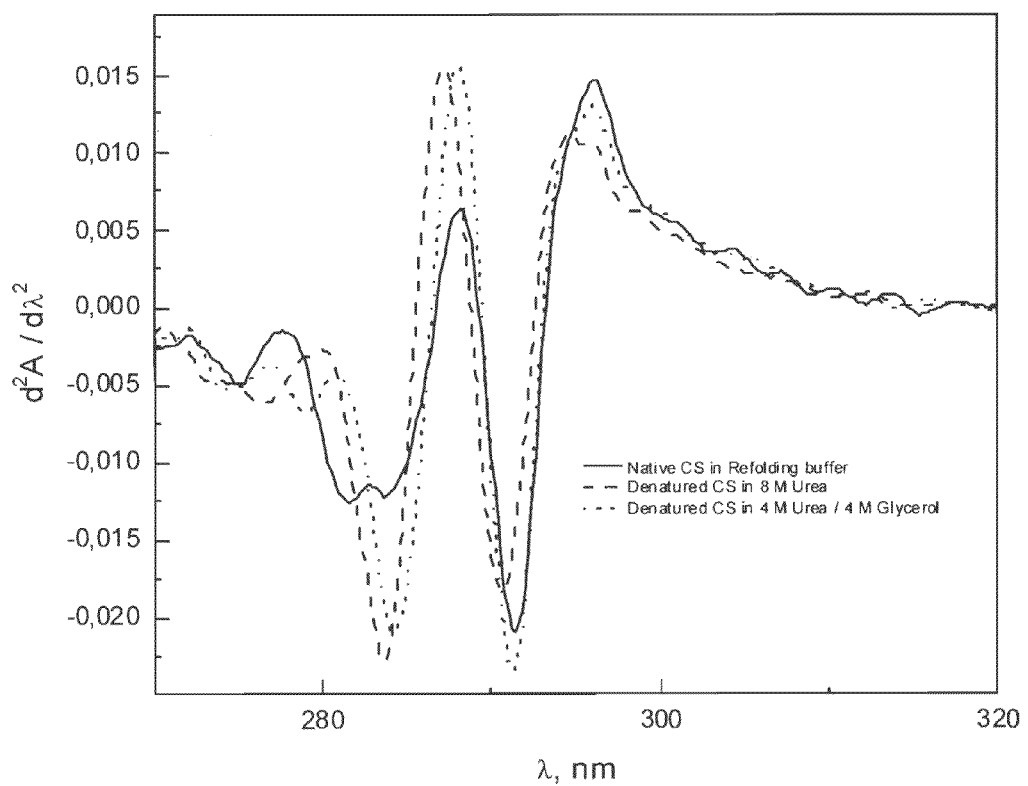
FIG. 10 is a second derivative absorbance spectra of citrate synthase in refolding buffer (solid line), in 8 M Urea—buffered (dashed line), and in mixture of 4 M Urea and 4 M Glycerol—buffered (dotted line). Protein concentration in the samples is 1 uM, pH of the buffer and osmolyte mixtures is 7.5.
Figure 11:
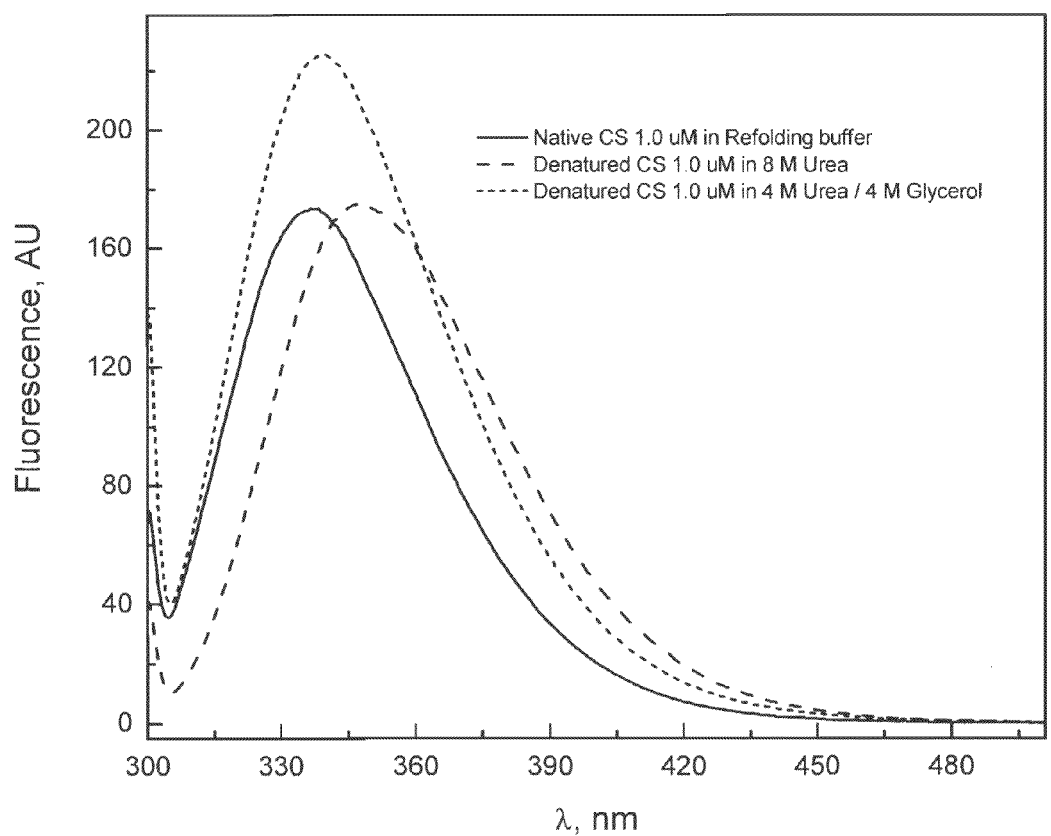
FIG. 11 is a fluorescence spectra of citrate synthase in refolding buffer (solid line), in 8 M Urea—buffered (dashed line), and in mixture of 4 M Urea and 4 M Glycerol—buffered (dotted line). Protein concentration in the samples is 1 uM, pH of the buffer and osmolyte mixtures is 7.5. Exitation wavelength is 295 nm, both, exitation and emission bandpass were 5 nm, scan speed is 60 nm/min.
Figure 12:
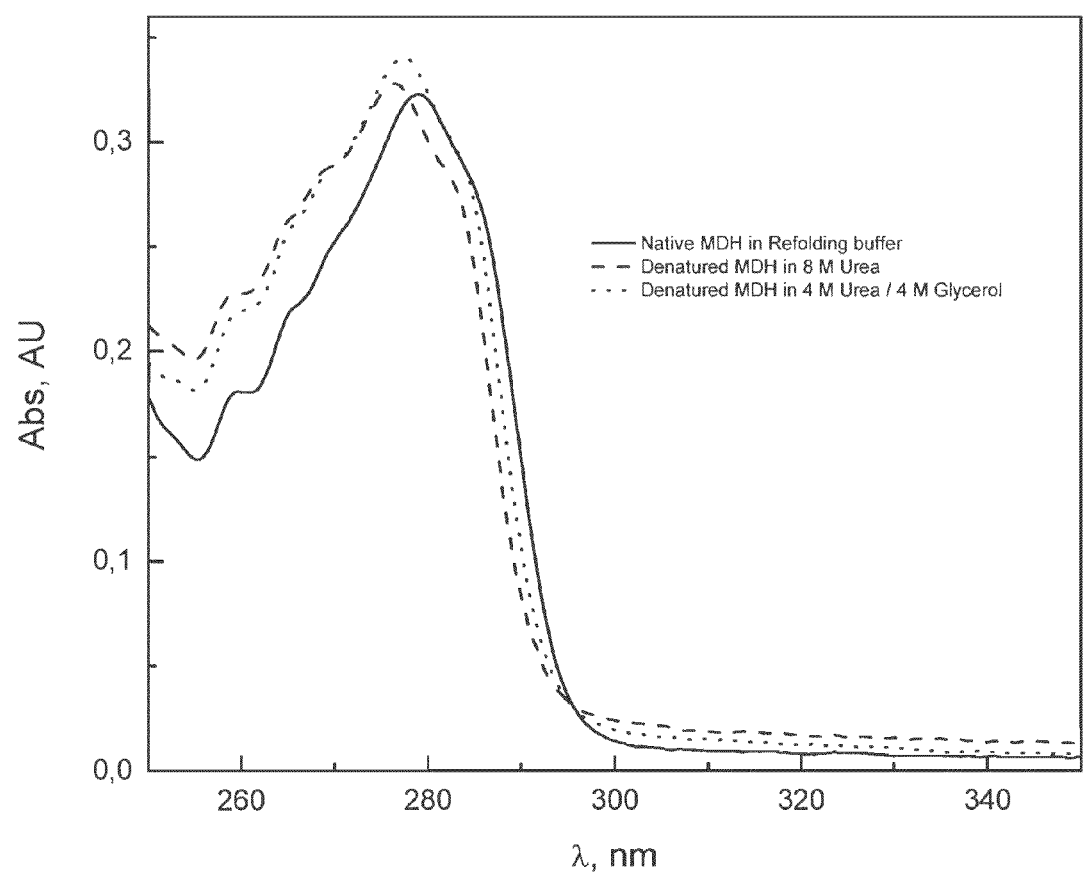
FIG. 12 is an absorbance spectra of malate dehydrogenase in refolding buffer (solid line), in 8 M Urea—buffered (dashed line), and in mixture of 4 M Urea and 4 M Glycerol—buffered (dotted line). Protein concentration in the samples is 5 uM, pH of the buffer and osmolyte mixtures is 7.5.
Figure 13:
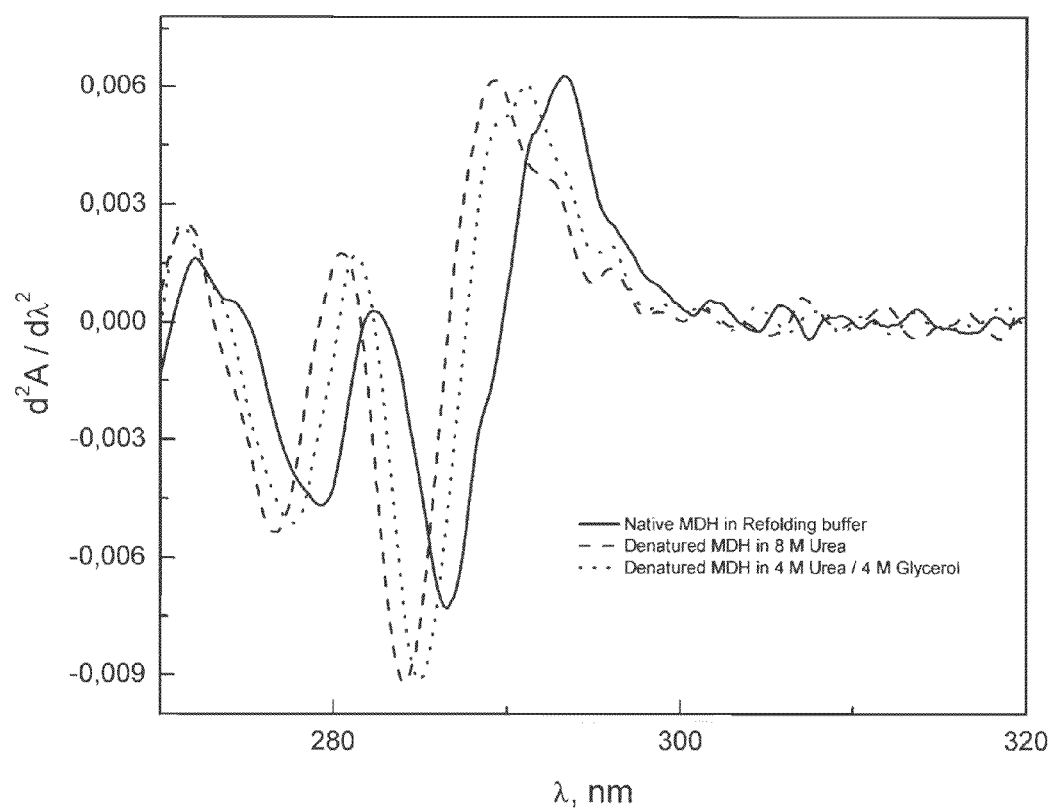
FIG. 13 is a second derivative absorbance spectra of malate dehydrogenase in refolding buffer (solid line), in 8 M Urea—buffered (dashed line), and in mixture of 4 M Urea and 4 M Glycerol—buffered (dotted line). Protein concentration in the samples is 5 uM, pH of the buffer and osmolyte mixtures is 7.5.
Figure 14:
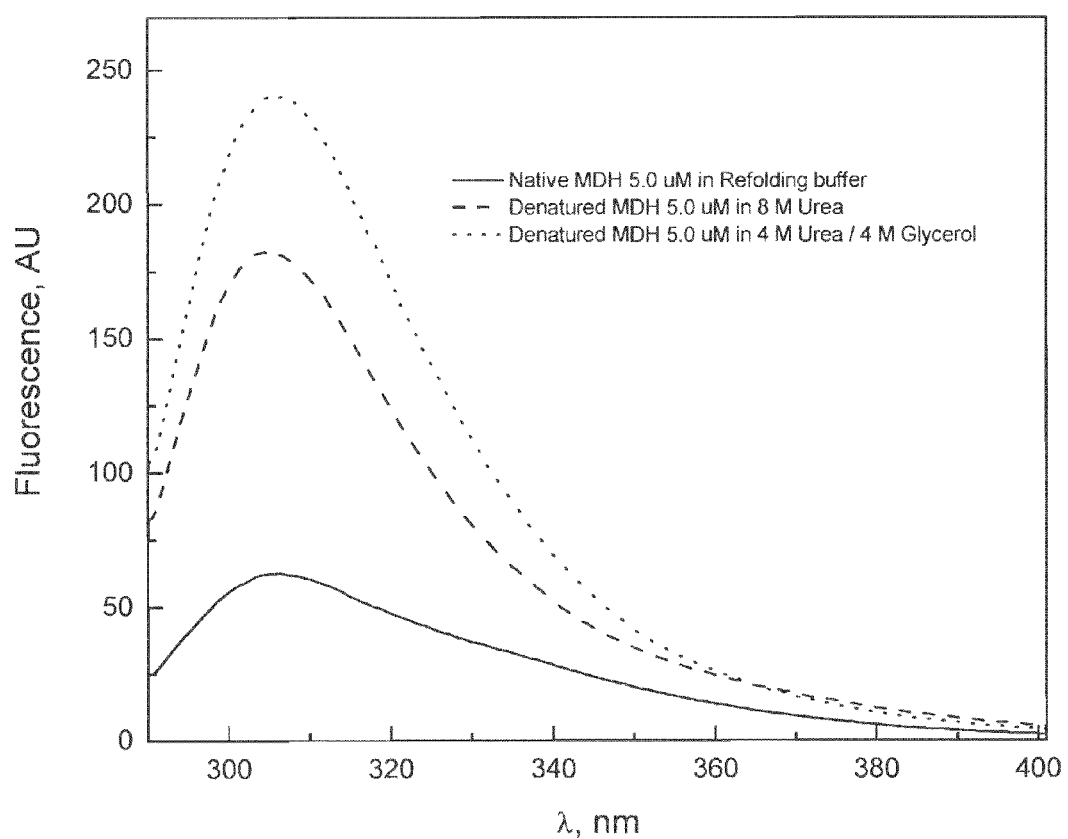
FIG. 14 is a fluorescence spectra of malate dehydrogenase in refolding buffer (solid line), in 8 M Urea—buffered (dashed line), and in mixture of 4 M Urea and 4 M Glycerol—buffered (dotted line). Protein concentration in the samples is 5 uM, pH of the buffer and osmolyte mixtures is 7.5. Exitation wavelength is 277 nm, both, exitation and emission bandpass were 5 nm, scan speed is 60 nm/min.

Based on the foregoing examples, it was believed that the structures of the long term folding intermediates for both citrate synthease (CS) and malate dehydrogenase (MDH) in osmolyte mixtures will show different perhaps intermediate spectral characteristics from the native active folded states and the completely unfolded inactive states. Thus, the inactive yet recoverable folding intermediate in osmolyte mixtures will show global spectroscopic characteristics of fluorescence emission, absorbance UV-visible spectra and second derivative UV-visible spectra that will reflect these unique characteristics (i.e., stable partially folded intermediates). In FIGS. 9-11, the absorbance, second derivative fingerprint, and fluorescence spectra, of the same concentration of CS were measured, examined and co-plotted. It is readily apparent that the spectra of the osmolyte mixture intermediate was significantly different from either the wild type (fully folded and active) or completely denatured spectra (completely unfolded) in every instance. Likewise, the same spectral characteristics (i.e., clear differences in entire spectra in the comparative spectra) were also evident from the spectra collected for malate dehydrogenase (FIGS. 12-14). It should be noted that the spectral characteristics of model compound aromatic residues (N-acetyl tryptophanamide and N-acetyltyrosine amide failed to replicate the spectra observed in the partially folded intermediate spectra, ruling out the possibility that these differences in the various spectra are simply due to solvation differences. It is more than likely that the nature of the inactive folding intermediate in osmolyte mixtures is indeed a different population of folds (i.e., a fluctuating mixture of locally folded and unfolded conformers). As indicated previously, this intermediate has the unique characteristics of not aggregating nor refolding, yet this intermediate can still be captured after a long incubation by the chaperonin once the folding intermediate is annealed onto the GroEL binding site using the methods outlined in FIG. 1. The metastable intermediates generated in our unique and never before characterized osmolyte mixture systems will most definitely be enormously useful in all aspects of protein folding, and stability formulations, particularly for both all protein based academic science and industrial endeavors.

While the present invention has been described herein with reference to the particular embodiments thereof, a latitude of modifications, various changes and substitutions are intended in the foregoing disclosure, and it will be appreciated that some features of the invention will be employed without a corresponding use of other features, without departing from the scope of the invention as set forth. From the foregoing, it will be seen that this invention is one well adapted to attain all ends and objectives herein-above set forth, together with the other advantages which are obvious and which are inherent to the invention. Since many possible embodiments may be made of the invention without departing from the scope thereof, it is to be understood that all matters herein set forth are to be interpreted as illustrative, and not in a limiting sense.

What is claimed and desired to be secured by Letters Patent is as follows:

1. A method of screening for a stabilizing osmolyte composition for an partially unfolded intermediate polypeptide of a polypeptide, comprising the steps of:

(a) providing an array having a plurality of elements with each element having a different test stabilizing osmolyte composition therein;
(b) introducing said polypeptide in a completely unfolded state which is capable of binding to a chaperonin to each element to form a polypeptide and test stabilizing osmolyte composition for said partially unfolded intermediate polypeptide;
(c) introducing, after a time delay, said chaperonin into each element;
(d) replacing said test stabilizing osmolyte composition with a refolding buffer so that said chaperonin can capture said partially unfolded intermediate polypeptide;
(e) adding at least one folding osmolyte into each element;
(f) measuring a yield of active polypeptides within each element by assaying for functional activity; and
(g) identifying said stabilizing osmolyte composition for said partially unfolded intermediate polypeptide, said stabilizing osmolyte composition being selected from the different test stabilizing osmolyte compositions in said plurality of elements, by measuring the yield of active polypeptides within each element of said array.

2. The method of screening of claim 1 wherein said partially unfolded intermediate polypeptide is incapable of being folded to its biologically active form by either a chaperonin or a folding osmolyte alone.

3. The method of screening of claim 1 wherein said chaperonin is of the *Escherichia coli* GroE chaperonin family.

4. The method of screening of claim 3 in which the chaperonin is *E. coli* GroEL.

5. The method of screening of claim 1 in which one of said different test stabilizing osmolyte composition comprises 2 M to 6 M glycerol and 2 M to 6 M urea.

6. The method of screening of claim 1 further comprising the step of promoting the folding of said polypeptide to its native state by the addition of a co-chaperonin to each of said elements, wherein said co-chaperonin has the ability to bind and dissociate from the chaperonin and aid said chaperonin to achieve correct binding of said polypeptide.

7. The method of screening of claim 1 wherein said identifying step comprises monitoring an enzymatic activity of said polypeptide.

8. The method of screening of claim 1 further comprising the step of adding a nucleotide to each of said elements.

9. The method of screening of claim 8 wherein said nucleotide is selected from the group consisting of ATP or ADP.

10. The method of screening of claim 1 wherein said time delay is 1 to 10 minutes.

11. The method of screening of claim 1 wherein said steps (a) to (g) are repeated.

12. The method of screening of claim 1 wherein said chaperonin is immobilized on a solid support.

13. The method of screening of claim 1 wherein said polypeptide in said introducing step (b) is completely unfolded with urea or guanidine hydrochloride.

14. The method of screening of claim 1 in which one of said different test stabilizing osmolyte compositions comprises 3 to 5 M glycerol and 4 to 5 M urea.

15. The method of screening of claim 1 wherein said partially unfolded intermediate polypeptide retains some native secondary and tertiary structure and is not aggregated.

16. The method of screening of claim 1 wherein said partially unfolded intermediate polypeptide is either malate dehydrogenase or citrate synthase.

17. The method of screening of claim 1 wherein said time delay is up to 24 hours.

* * * * *